United States Patent
Lemmens et al.

(10) Patent No.: US 10,004,919 B2
(45) Date of Patent: Jun. 26, 2018

(54) PHOTOTHERAPY PATCH WITH INCREASED THERMAL INSULATION

(71) Applicant: KONINKLIJKE PHILIPS N.V., Eindhoven (NL)

(72) Inventors: Paul Marcel Carl Lemmens, Eindhoven (NL); Gerrit Oversluizen, Eindhoven (NL); Wouter Hendrik Cornelis Spoorendonk, Eindhoven (NL); Jacobus Petrus Johannes Van Os, Eindhoven (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 0 days. days.

(21) Appl. No.: 14/411,750

(22) PCT Filed: Jun. 25, 2013

(86) PCT No.: PCT/IB2013/055200
§ 371 (c)(1),
(2) Date: Dec. 29, 2014

(87) PCT Pub. No.: WO2014/006537
PCT Pub. Date: Jan. 9, 2014

(65) Prior Publication Data
US 2015/0165228 A1 Jun. 18, 2015

Related U.S. Application Data

(60) Provisional application No. 61/667,494, filed on Jul. 3, 2012.

(51) Int. Cl.
*A61N 5/06* (2006.01)

(52) U.S. Cl.
CPC ......... *A61N 5/0613* (2013.01); *A61N 5/0616* (2013.01); *A61N 5/0625* (2013.01); *A61N 2005/0626* (2013.01); *A61N 2005/0645* (2013.01); *A61N 2005/0652* (2013.01); *F04C 2270/0421* (2013.01)

(58) Field of Classification Search
CPC .. A61N 5/0613; A61N 5/0616; A61N 5/0622; A61N 5/0624; A61N 5/0625; A61N 5/0626; A61N 5/0627; A61N 5/0632; A61B 18/18; A61B 18/2013; A61B 2018/00452;
(Continued)

(56) References Cited

U.S. PATENT DOCUMENTS 6,290,713 B1 9/2001 Russell
7,210,817 B2 5/2007 Lee
(Continued)

FOREIGN PATENT DOCUMENTS

CN 201805961 U 4/2011
JP 06459 A 1/1994
(Continued)

*Primary Examiner* — Ahmed Farah

(57) ABSTRACT

A light emitting device for application near mammal tissue includes a flexible body having a front surface for facing the mammal tissue and an opposing back surface. The flexible body accommodates at least one light source which is arranged for irradiating an irradiation area of the mammal tissue. A thermally insulating layer covers the back surface of the flexible body. The thermally insulating layer has a larger surface area than the flexible body.

16 Claims, 3 Drawing Sheets

(58) Field of Classification Search
CPC .. A61B 2018/00636; A61B 2018/0066; A61B 2018/2015; A61B 2018/2023
USPC .................. 607/88–92; 606/9–12; 128/898
See application file for complete search history.

(56) References Cited

U.S. PATENT DOCUMENTS

| | | | |
|---|---|---|---|
| 2007/0179570 A1* | 8/2007 | De Taboada | A61H 7/006 607/88 |
| 2007/0233208 A1 | 10/2007 | Kurtz | |
| 2010/0179469 A1* | 7/2010 | Hammond | A61N 5/0603 604/20 |
| 2011/0144727 A1 | 6/2011 | Benedict | |
| 2012/0078329 A1 | 3/2012 | Shimada | |
| 2013/0304019 A1* | 11/2013 | Cooper | A61N 5/062 604/501 |
| 2014/0163664 A1* | 6/2014 | Goldsmith | A61B 17/00491 623/1.11 |
| 2014/0303697 A1* | 10/2014 | Anderson | A61B 18/02 607/104 |
| 2015/0039060 A1 | 2/2015 | Paulussen et al. | |

FOREIGN PATENT DOCUMENTS

| | | |
|---|---|---|
| JP | 0712153 U | 2/1995 |
| JP | 1012153 U | 2/1995 |
| JP | 11192315 A | 7/1999 |
| JP | 2012090950 A | 5/2012 |
| RU | 49454 U1 | 11/2005 |
| RU | 111438 U1 | 12/2011 |
| WO | 2012037355 A2 | 3/2012 |
| WO | 2012085801 A1 | 6/2012 |
| WO | 2012172456 A2 | 12/2012 |

* cited by examiner

PHOTOTHERAPY PATCH WITH INCREASED THERMAL INSULATION

CROSS-REFERENCE TO PRIOR APPLICATIONS

This application is the U.S. National Phase application under 35 U.S.C. § 371 of International Application No. PCT/IB2013/055200, filed on Jun. 25, 2013, which claims the benefit of U.S. Provisional Patent Application No. 61/667,494, filed on Jul. 3, 2013. These applications are hereby incorporated by reference herein.

FIELD OF THE INVENTION

The present invention relates to light therapy devices for use near mammal tissue. More specifically, the present invention relates to light therapy devices for use as pain relief patch, a kit of part for manufacturing such a patch and to a method for its assembly.

BACKGROUND OF THE INVENTION

For a portable device, power consumption is a key design factor. More particularly, for portable and wearable devices that uses high intensity light for treatment, for example from high power LEDs, battery consumption is even more important, because the high intensity light requires considerable power. Moreover, such a portable device must be able to meet such high power requirements for longer periods of time during subsequent application sessions of light therapy without recharging. In addition, in order to make the device wearable, these requirements must be fitted in a small form factor.

In a number of light therapy treatments, it is effective to activate bodily processes that trigger vasodilation. Vasodilation is part of the body thermo regulatory system and is considered beneficial for wound healing, pain relief, and dermal health.

A further problem of light therapy devices that treat, for instance, muscle pain using light, is that light source produce heat. In prior art, this problem is solved by using heat sinking as, e.g., in U.S. Pat. No. 6,290,713 where the illuminator is passively or actively cooled, so that the skin contact surface remains below a desired temperature. A passive cooling is presented as a fin positioned to provide increased transfer of heat produced by the LEDs away from the skin of the patient. To further protect the patient from the heat produced by the LED light source, U.S. 2010/179469 uses an insulation layer between the portion adapted to contact the skin of a patient and the light source. U.S. 2010/179469 further suggests adjusting the heat using a heat management system to prevent overheating of the patient, for example, by increasing a coolant supply or the speed of a fan.

To some extent, power consumption of light therapy devices may be reduced by pulsing the LED instead of continuously driving the LED, while still creating an effect of vasodilation production, since vasodilation is activated via heat receptors located in the skin which may be triggered by a relatively short, but powerful burst of light. Once it is activated, it will remain active for a relatively long period of time, in the order of several minutes, without the need for further heat stimulus. However, another problem may appear because the user may experience the periods between light pulses as cold, making the device uncomfortable to use.

SUMMARY OF THE INVENTION

It is an object of the present invention to improve the current state of the art by addressing at least one of the concerns identified above.

In a first aspect of the invention a light emitting device is provided for application near mammal tissue, comprising: a flexible body having a front surface for facing said mammal tissue and an opposing back surface, said flexible body accommodating at least one light source, wherein said at least one light source is arranged for irradiating an irradiation area of said mammal tissue; and a thermally insulating layer covering the back surface of the flexible body, wherein the thermally insulating layer has a larger surface area than the flexible body.

By insulating the light emitting device, the heat from the light source is (re)used in the therapeutic treatment. Heat may be beneficial in a lot of therapeutic treatments, e.g. in the relief of pain, and is beneficial for the vasodilation production. Tests have shown that a substantial amount of the heat generated by light emitting device is dissipated via the skin. Experimentation also shows that insulating the patch does not dramatically increase the heat load on the skin. To the contrary, insulation keeps the heat in the patch and ensures a longer lasting warmth sensation that is beneficial both on a physical/physiological level and on a psychological level. Furthermore, the overall power usage of the light source may be reduced and hence battery lifetime for the light emitting device can be increased.

A further surprising effect is that, with an identical irradiation, the skin temperature does not increase more or faster with increasing insulation. The temperature increase rate is even decreased, opposite to what may be expected. The reason for this surprising effect is that the vasodilation is increased, thus carrying away more heat from the irradiation area and thus decreasing the temperature increase rate. This allows application of larger irradiances for light induced treatment without jeopardizing skin safety i.e. while keeping skin temperature within safe ranges. Therefore, increasing the insulation of light emitting phototherapy device has many beneficial effects, such as enabling higher irradiances, increasing vasodilation, increasing treatment duration, decreasing power consumption/requirements and prolonging battery life.

The thermal insulation also makes the treatment less affected by the ambient environment. The results from using the device will thus be more predictable, since they are not affected by e.g. ambient temperature, thickness of clothes worn by the user and covering the device, etc.

The thermal insulating layer of the light emitting device may have an insulation value defined by a Thermal Overall Grade (TOG), a British Standard 4745 used in the blanket/clothing fabric industry. Typically a 2 to 3 mm thick fleece blanket provides a thermal insulation value of 0.5 TOG corresponding to 0.05 m2K/W. For the light emitting device according to embodiments of the invention a TOG of the insulation layer of over 0.2, preferably over 0.4, more preferably over 0.5 has proven efficient, for reasons described above.

The light source of the light emitting device is preferably a LED, although it could be a light source in the group consisting of: LED, incandescent lamp, and gas discharge lamp. The advantages of using a LED or LEDs are that they are energy efficient and often narrow in their radiation spectrum, which again helps reducing energy consumption since the output power is substantially generated in the desired wavelength range(s) for the treatment.

In an embodiment, the light source is a number of LEDs distributed over a light emitting area corresponding to the irradiation area. They may, e.g., be distributed as a matrix over the light emitting area. An LED matrix, being a (assembled) large area light source, makes it possible to treat an equally large area of the mammal tissue without using bulky and/or complicated optics for spreading radiation from a single light source across the radiation area.

The light emitting device may further comprise a control unit for controlling the light source output. According to an embodiment, the control unit is arranged to drive the light source according to predetermined schemes of cony and 'off' intervals. As the insulation layer reduces heat losses, temperature drops during the 'off' period of the light source or hot spots during the cony period of the light source can be significantly reduced. This allows further reducing a duty cycle of the light source interval driving scheme, i.e. using shorter 'on' periods and longer 'off' periods, making the light emitting device even more power efficient and thus power saving. For example, the control unit is configured to control a light source output to drive the light source according to predetermined intervals of light emission, where a duration of the predetermined intervals is based on the insulation value of the thermally insulating layer. In the context of this application, a cony period refers to a period in which the light source is driven to emit light at an irradiance level sufficient to trigger a vasodilation process in the mammal tissue and a 'off' period refers to a period in which the light source is driven to emit light at an irradiance level insufficient to trigger a vasodilation response in the mammal tissue. 'Off' therefore does not necessarily equal to 'no light'.

The thermal insulating layer may be made of a material comprised in the group consisting of materials combining low weight, low heat capacity, and high insulation.

Examples of such materials are textiles and foam.

In an embodiment, the insulating layer has a surface area that is at least 150% the surface area of the lighting area, more preferable at least 200% of the surface area of the light emitting area. This ensures that the insulating properties and the advantages discussed above are fully achieved and the benefits of the insulation are enhanced. Providing an insulation layer that is substantially larger than the light emitting area has the advantage that, in addition to insulating the flexible body accommodating the light source(s), it also insulated a substantial area of the mammal tissue from the ambient and hence helps sustaining the warmth effect across a substantial larger area than the light emitting area itself.

Said insulating material may be a light weight material for comfort of use.

The light emitting device according to the invention may be used on a human, but the same effects and most of the advantages are present also when used on any mammal.

In a further aspect of the invention a kit of parts for manufacturing a light emitting device for application near mammal tissue is provided, the kit of parts comprising: a flexible body having a front surface for facing said mammal tissue and an opposing back surface, said flexible body accommodating at least one light source wherein said at least one light source is arranged for irradiating an irradiation area of said mammal tissue; and a thermally insulating cover adapted to cover the back surface of the flexible body, wherein the thermally insulating cover has a larger surface area than the flexible body.

It is obvious for a person skilled in the art that the kit of parts may be embodied in the same way as the light emitting device described above, and has the same corresponding advantages.

In a third aspect of the invention, a method for assembling a light emitting device for application near mammal tissue is provided, comprising the steps of: providing a flexible body having a front surface for facing said mammal tissue and an opposing back surface, said flexible body accommodating at least one light source wherein said at least one light source is arranged for irradiating an irradiation area of said mammal tissue; and covering the back surface of the flexible body with a thermally insulating cover, wherein the thermally insulating cover has a larger surface area than the flexible body.

It should be noted that the inventive method may incorporate any of the features described above in association with the inventive light emitting device and has the same corresponding advantages. It is further noted that the invention relates to all possible combinations of features recited in the claims.

The invention is advantageously used in applications where heat is considered to have an additional or even synergetic effect on top of the effect of light emitted from the light emitting device onto the mammal tissue. Examples of such application include pain relief, wound healing, or applications where the soothing effect of warmth on the mammal tissue being treated may provide an advantageous. The invention may therefore also be used in applications where the main objective is to generate heat and apply heat to the mammal tissue, in which case the light source is a source of heat and the light emission itself is subordinate e.g. IR LEDs may be used.

BRIEF DESCRIPTION OF THE DRAWINGS

The above objects, as well as additional objects, features and advantages of the present invention, will be more fully appreciated by reference to the following illustrative and non-limiting detailed description of preferred embodiments of the present invention, when taken in conjunction with the accompanying drawings, wherein.

As illustrated in the figures, the sizes of layers and regions are exaggerated for illustrative purposes and, thus, are provided to illustrate the general structures of embodiments of the present invention. Like reference numerals refer to like elements throughout.

DETAILED DESCRIPTION OF THE EMBODIMENT

Figure 1:
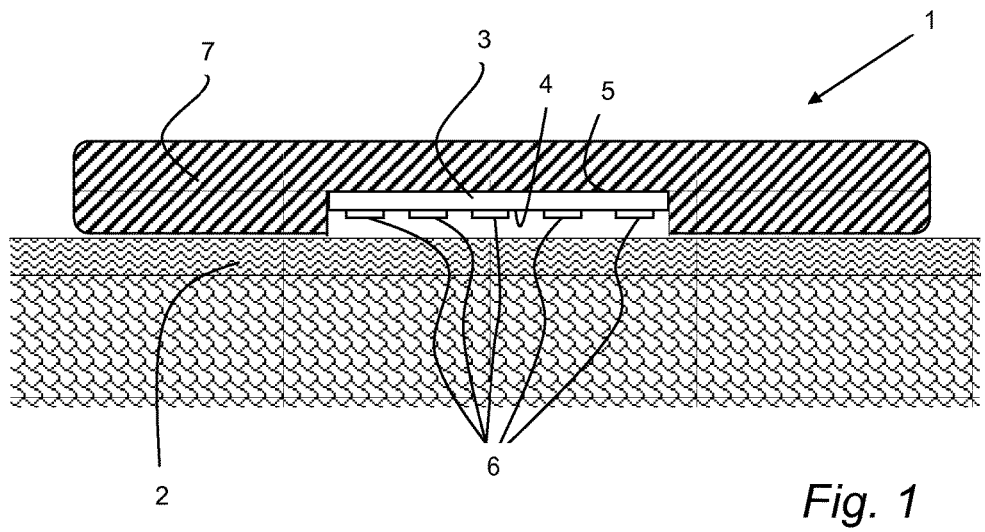
FIG. 1 is a cross sectional image of an insulated light emitting device according to the invention.

FIG. 1 shows a cross sectional view of an embodiment of the lighting device according to the present invention. The lighting device 1 is built up by a flexible body 3 having a front surface 4 and a back surface 5. A light source 6 is attached to the front side 4 in the form of a LED matrix, facing the mammal tissue 2, usually skin. Alternatively the light source may be incorporated or embed in the flexible body or be attached to the back surface of the flexible body and irradiate through the flexible body in the direction of the mammal tissue 2. The flexible body 3 with the light source 6 is covered by or embedded in a thermally insulating layer 7, so that the device and the tissue 2, covered by the device, are thermally insulated from the environment. The light source is located so as to radiate the tissue 2 without touching it directly. The thermal insulation layer is typically 2-4 mm thick and preferably has a thermal insulation of 0.5 TOG (thermal overall grade) or more, corresponding to 0.05 $m^2K/W$ or more.

Figure 2A:
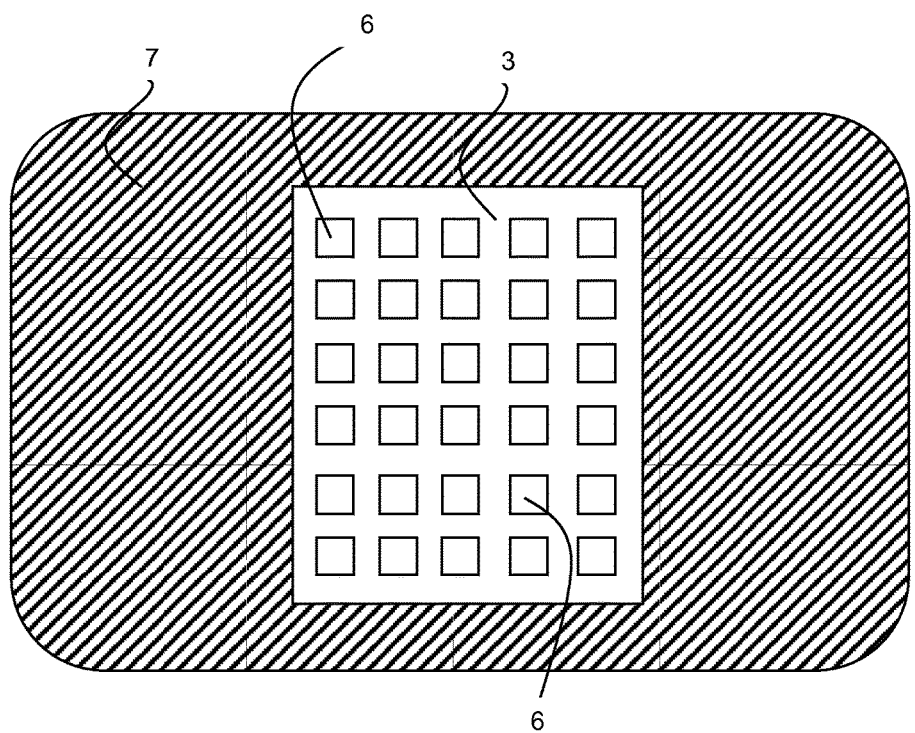
FIG. 2a is a schematic image of an insulated light emitting device according to the invention.
Figure 2B:
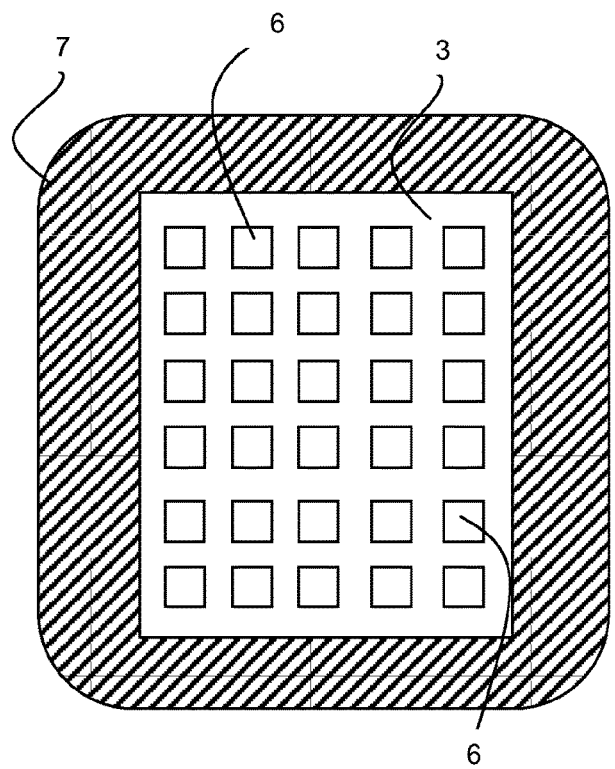
FIG. 2b is a schematic image of another embodiment of an insulated light emitting device according to the invention.

FIG. 2a shows the light emitting device 1 from the front side 4, the side on which the light source, i.e. the LED matrix, is located. FIG. 2a shows an embodiment where the size of the insulating layer is much larger than that of the irradiating area. FIG. 2b shows another embodiment of the device where the size of the insulating layer is only slightly larger than that of the irradiation area. This embodiment may be used if a small device is required, e.g., if a bigger device does not fit the area of the tissue to be treated.

Figure 3:
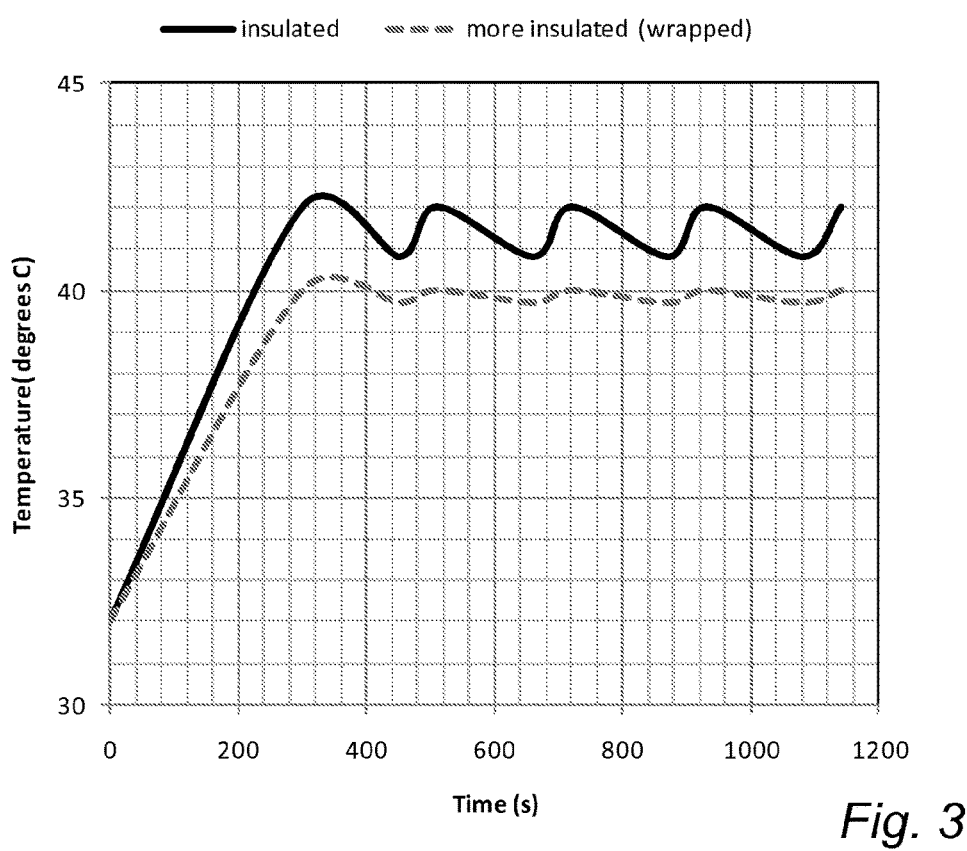
FIG. 3 is a graph showing the effects of increasing the insulation of a light emitting device according to an embodiment of invention wherein an interval driven light source is used.

FIG. 3 shows the temperature response of the skin, using pulse driven light source incorporated in (i) an insulated light emitting device, e.g. a patch with a thermally insulating layer on the back of the patch (solid curve), and (ii) a further insulated light emitting device, e.g. the same patch wrapped around a body part and covered with an additional blanket (dashed curve). An increase of skin temperature corresponds to an on-period and a decrease of skin temperature corresponds to an off-period of the light source.

With increasing insulation, the temperature decrease in the off-period is reduced, allowing for longer off-periods. However, and this was not expected, also in the on-period the temperature increase reduced with increasing insulation. This is attributed to a systemic response of increased vasodilation. The increased vasodilation also results in a lower average temperature (41.5 degrees for insulated and 40 degrees for insulated+wrapped in FIG. 3). Consequently the irradiance level and therewith the light-induced effects in the tissue can be further increased without risks of skin burns.

Therefore, increasing the insulation has many beneficial effects, such as enabling increasing irradiance, increasing vasodilation, increasing treatment duration (longer off-times), decreasing power consumption/requirements and therefore prolonging battery life.

This device and accompanying method of using the device described above effectively reduce power consumption in portable and/or wearable devices, particularly those devices that support or trigger vasodilation processes in mammal tissue as part of the desired effect in for example the treatment of muscular pain, next to the photobiological light-induces effects of the light therapy. The On interval truly activates a vasodilation and photobiology response that lasts even after heat/light input has ceased during an Off interval. These effects are beneficial and efficacious for dermal health, wound healing, and pain relief.

Figure 4:
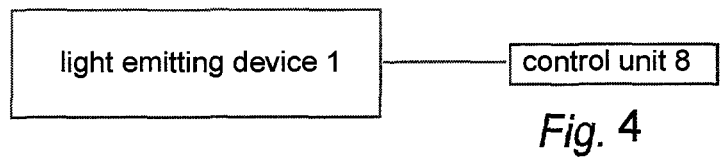
FIG. 4 is a block diagram showing a control unit connected to an insulted light emitting device according to an embodiment of the invention.

FIG. 4 shows a block diagram with a control unit 8 connected to the light emitting device 1. The control unit 8 is arranged to control a light source output of the light source 6 based on the insulation value of the thermally insulating layer 7.

It should be noted that the details of the assembly do not matter for the invention. It is understood that other variations of the present invention are contemplated and in some instances, some features of the invention can be employed without a corresponding use of other features. Accordingly, it is appropriate that the appended claims be construed broadly in a manner consistent with the scope of the invention.

Additionally, variations to the disclosed embodiments can be understood and effected by the skilled person in practicing the claimed invention, from a study of the drawings, the disclosure, and the appended claims. In the claims, the word "comprising" does not exclude other elements or steps, and the indefinite article "a" or "an" does not exclude a plurality. The mere fact that certain measures are recited in mutually different dependent claims does not indicate that a combination of these measures cannot be used to advantage.

The invention claimed is:

1. A light emitting device for application near a mammal tissue, comprising:
   a flexible body having a front surface for facing the mammal tissue and an opposing back surface, the flexible body having at least one light source, wherein the at least one light source is configured to irradiate an irradiation area of the mammal tissue;
   a thermally insulating layer covering the opposing back surface of the flexible body; and
   a control unit configured to control the at least one light source based on an insulation value of the thermally insulating layer.

2. The light emitting device according to claim 1, wherein the insulation value of the thermally insulating layer is defined by a Thermal Overall Grade (TOG) of at least 0.2.

3. The light emitting device according to claim 1, wherein the at least one light source is a LED.

4. The light emitting device according to claim 1, wherein the at least one light source comprises a plurality of LEDs distributed over a light emitting area facing the mammal tissue for irradiating the irradiation area.

5. The light emitting device according to claim 1, wherein the thermally insulating layer is made of a material comprising one of a textile and a foam.

6. The light emitting device according to claim 1, wherein the thermally insulating layer has a surface area that is more than twice a surface area of a light emitting area of the flexible body.

7. The light emitting device according to claim 6, wherein the thermally insulating material is a light weight material.

8. The light emitting device according to claim 1, wherein the device is adapted for pain relief.

9. The light emitting device according to claim 1, wherein the insulation value of the thermally insulating layer is defined by a Thermal Overall Grade (TOG) of at least 0.4.

10. The light emitting device according to claim 1, wherein the insulation value of the thermally insulating layer is defined by a Thermal Overall Grade (TOG) of at least 0.5.

11. The light emitting device according to claim 1, wherein the control unit is further configured to control a light source output of the at least one light source, wherein the control unit is configured to drive the at least one light source according to predetermined intervals of light emission, and wherein a duration of the predetermined intervals of light emission is based on the insulation value of the thermally insulating layer.

12. A light emitting device for application near a mammal tissue, comprising:
    a flexible body having a front surface for facing the mammal tissue and an opposing back surface, the flexible body having at least one light source, wherein the at least one light source is configured to irradiate an irradiation area of the mammal tissue;

a thermally insulating layer covering the opposing back surface of the flexible body; and a control unit for controlling a light source output of the at least one light source, wherein the control unit is configured to drive the at least one light source according to predetermined intervals of light emission, and wherein a duration of the predetermined intervals of light emission is based on an insulation value of the thermally insulating layer.

13. A kit of parts for manufacturing a light emitting device for application near a mammal tissue, the kit of parts comprising:

a flexible body having a front surface for facing the mammal tissue and an opposing back surface, the flexible body having at least one light source, wherein the at least one light source is configured to irradiate an irradiation area of the mammal tissue;

a thermally insulating cover configured to cover the opposing back surface of the flexible body; and a control unit configured to control the at least one light source based on an insulation value of the thermally insulating layer.

14. The kit of parts according to claim 13, wherein the control unit is further configured to control a light source output of the at least one light source, wherein the control unit is configured to drive the at least one light source according to predetermined intervals of light emission, and wherein a duration of the predetermined intervals of light emission is based on the insulation value of the thermally insulating layer.

15. A method of assembling a light emitting device for application near a mammal tissue, comprising acts of:

providing a flexible body having a front surface for facing the mammal tissue and an opposing back surface, the flexible body having at least one light source, wherein the at least one light source is configured to irradiate an irradiation area of the mammal tissue;

covering the opposing back surface of the flexible body with a thermally insulating cover; and operably connecting a control unit configured to control the at least one light source based on an insulation value of the thermally insulating layer.

16. The method according to claim 15, wherein the wherein the control unit is configured to control a light source output of the at least one light source by driving the at least one light source according to predetermined intervals of light emission, and wherein a duration of the predetermined intervals of light emission is based on the insulation value of the thermally insulating layer.

* * * * *